US009278917B2

(12) United States Patent
Remarchuk

(10) Patent No.: US 9,278,917 B2
(45) Date of Patent: Mar. 8, 2016

(54) PROCESS FOR MAKING AMINO ACID COMPOUNDS

(71) Applicant: Genentech, Inc., South San Francisco, CA (US)

(72) Inventor: Travis Remarchuk, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 14/401,095

(22) PCT Filed: May 17, 2013

(86) PCT No.: PCT/US2013/041687
§ 371 (c)(1),
(2) Date: Nov. 13, 2014

(87) PCT Pub. No.: WO2013/173779
PCT Pub. Date: Nov. 21, 2013

(65) Prior Publication Data
US 2015/0148559 A1 May 28, 2015

Related U.S. Application Data

(60) Provisional application No. 61/648,534, filed on May 17, 2012.

(51) Int. Cl.
| C07C 229/30 | (2006.01) |
| C07C 269/06 | (2006.01) |
| C07C 271/22 | (2006.01) |
| C07C 67/343 | (2006.01) |
| C07C 67/313 | (2006.01) |
| C07C 269/04 | (2006.01) |

(52) U.S. Cl.
CPC ............ *C07C 269/06* (2013.01); *C07C 67/313* (2013.01); *C07C 67/343* (2013.01); *C07C 229/30* (2013.01); *C07C 269/04* (2013.01); *C07C 271/22* (2013.01); *C07B 2200/07* (2013.01)

(58) Field of Classification Search
CPC .. C07C 269/04; C07C 269/06; C07C 229/30; C07C 67/313; C07C 67/343; C07C 271/22; C07B 2200/07
See application file for complete search history.

(56) References Cited

U.S. PATENT DOCUMENTS

| 4,663,327 A | 5/1987 | Sasse et al. |
| 7,169,928 B2 | 1/2007 | Schwartz et al. |
| 8,063,050 B2 | 11/2011 | Mitchell et al. |
| 2008/0262020 A1 | 10/2008 | Muneaux et al. |
| 2011/0281844 A1 | 11/2011 | Schwartz et al. |
| 2012/0149684 A1 | 6/2012 | Beight et al. |
| 2014/0121193 A1 | 5/2014 | Katz et al. |
| 2015/0099880 A1 | 4/2015 | Babu et al. |
| 2015/0099881 A1 | 4/2015 | Lane et al. |

FOREIGN PATENT DOCUMENTS

| WO | 9515684 A1 | 6/1995 |
| WO | 9844797 A1 | 10/1998 |
| WO | 9856234 A1 | 12/1998 |
| WO | 0052134 A2 | 9/2000 |
| WO | 0122963 A1 | 4/2001 |
| WO | 2004108673 A2 | 12/2004 |
| WO | WO 2008/006040 A1 | 1/2008 |
| WO | 2009047255 A1 | 4/2009 |
| WO | 2010120935 A1 | 10/2010 |
| WO | 2012009649 A1 | 1/2012 |
| WO | 2012040258 A2 | 3/2012 |
| WO | 2012177925 A1 | 12/2012 |
| WO | 2014127350 A1 | 8/2014 |
| WO | 2014150395 A1 | 9/2014 |

OTHER PUBLICATIONS

Davies et al., "Structure-Activity Relationships of the Peptide Deformylase Inhibitor BB-3497: Modification of the Methylene Spacer and the P1' Side Chain", *Bioorganic & Medicinal Chemistry Letters 13*, 2709-2713 (2003).
Davies et al., "Catalytic Enantioselective Synthesis β-Amino Acids", *Angew. Chem. 114* (12), 2301-2303 (2002).
Elaridi et al., "An enantioselective synthesis of β2-amino acid derivatives", *Tetrahedron: Asymmetry 16*, 1309-1319 (2005).
Jiang et al., "Investigation of the Transition-Metal- and Acid-Catalyzed Reactions of β-(N-Tosyl)amino Diazo Carbonyl Compounds", *J. Org. Chem. 68*, 893-900 (2003).
Patent Cooperation Treaty, International Searching Authority, Search Report and Written Opinion for PCT/US2013/041687, 11 pages, Jun. 19, 2013.

*Primary Examiner* — Shailendra Kumar
(74) *Attorney, Agent, or Firm* — Viksnins Harris & Padys PLLP

(57) ABSTRACT

The invention provides new processes for making and purifying amino acid compounds, which are useful in the preparation of AKT inhibitors used in the treatment of diseases such as cancer, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

21 Claims, 1 Drawing Sheet

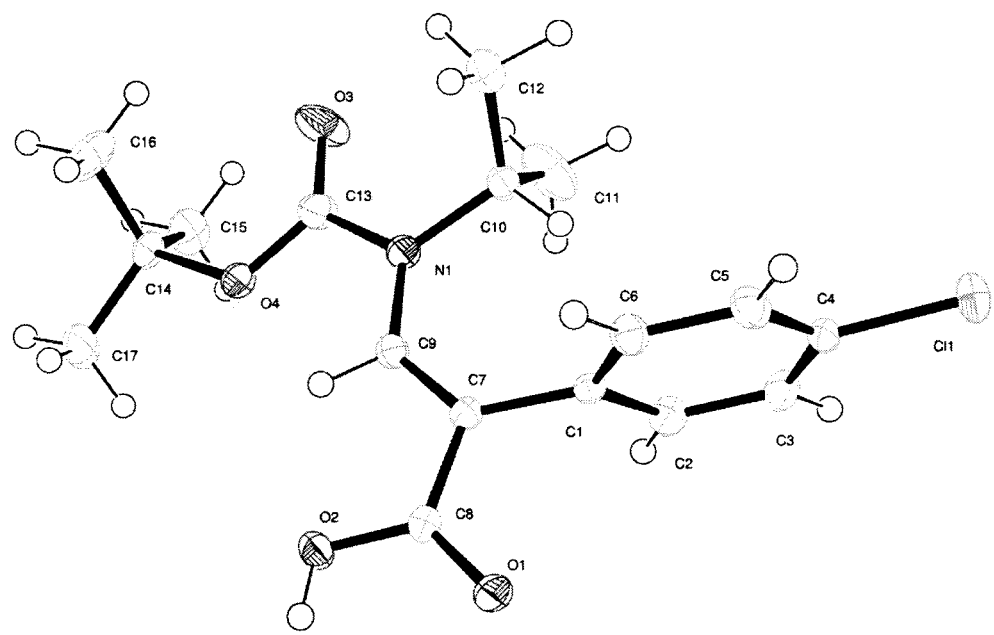

PROCESS FOR MAKING AMINO ACID COMPOUNDS

PRIORITY OF INVENTION

This application is a 371 of PCT/US2013/041687, filed on May 17, 2013, which claims priority to U.S. Provisional Application No. 61/648,534 that was filed on 17 May 2012. The entire content of this provisional application is hereby incorporated herein by reference.

FIELD OF THE INVENTION

Disclosed herein are processes for making and purifying amino acid compounds for the synthesis of inhibitors of AKT kinase activity.

BACKGROUND OF THE INVENTION

The Protein Kinase B/Akt enzymes are a group of serine/threonine kinases that are overexpressed in certain human tumors. International Patent Application Publication Number WO 2008/006040 and U.S. Pat. No. 8,063,050 discuss a number of inhibitors of AKT, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (GDC-0068). While processes described in WO 2008/006040 and U.S. Pat. No. 8,063,050 are useful in providing hydroxylated cyclopenta[d]pyrimidine compounds as AKT protein kinase inhibitors, alternative or improved processes are needed, including for large scale manufacturing of these compounds.

BRIEF SUMMARY OF THE INVENTION

Disclosed are processes for preparing, separating and purifying compounds detailed herein. Compounds provided herein include AKT protein kinase inhibitors, salts thereof, and intermediates useful in the preparation of such compounds.

One aspect includes a process comprising reducing a compound of formula II, or a salt thereof:

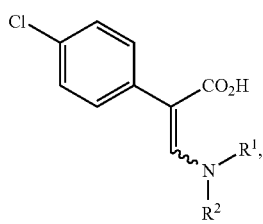

II wherein $R^1$ and $R^2$ are defined herein to form a compound of formula I:

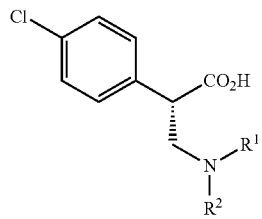

I or a salt thereof.

Another aspect includes a process comprising hydrolysing a compound of formula III, or salt thereof:

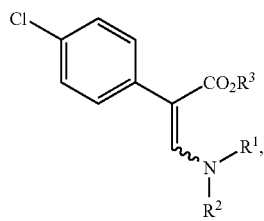

III wherein $R^3$ is defined herein to form a compound of formula II or salt thereof.

Another aspect includes a process comprising reacting a compound of formula IV, or a salt or tautomer thereof:

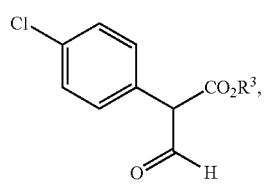

IV with —$NHR^1R^2$ or a salt thereof, to form a compound of formula III, or a salt thereof.

Another aspect includes a process comprising contacting a compound of formula V or a salt thereof,

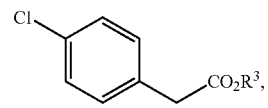

V with $HCO_2R^4$, wherein $R^4$ is defined herein, to form a compound of formula IV, or a salt thereof.

3

Another aspect includes a compound of formula VI:

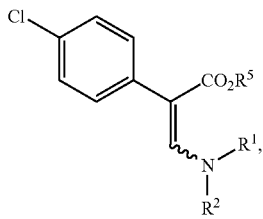

or salt thereof, wherein $R^1$, $R^2$ and $R^5$ are defined herein.

Another aspect includes a compound having the formula VIa:

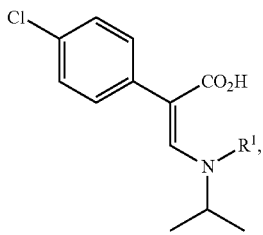

or a salt thereof, wherein $R^1$ is defined herein.

Another aspect includes a compound having the formula VIb:

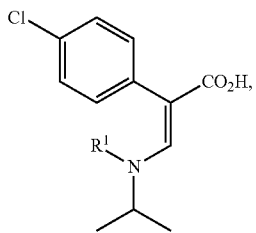

or a salt thereof, wherein $R^1$ is defined herein.

BRIEF DESCRIPTION OF THE FIGURES

FIG. 1 shows the solved single crystal x-ray analysis of (E)-3-(tert-butoxycarbonyl(isopropyl)amino)-2-(4-chlorophenyl)acrylic acid, which shows the E-configuration.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. In the event that one or more of the incorporated literature and similar materials differs from or contradicts this application, including but not limited to defined terms, term usage, described techniques, or the like, this application controls.

4

"Acyl" means a carbonyl containing substituent represented by the formula —C(O)—R in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are independently optionally substituted and as defined herein. Acyl groups include alkanoyl (e.g., acetyl), aroyl (e.g., benzoyl), and heteroaroyl (e.g., pyridinoyl).

The term "alkyl" as used herein refers to a saturated linear or branched-chain monovalent hydrocarbon radical of one to twelve carbon atoms, and in another embodiment one to six carbon atoms, wherein the alkyl radical may be optionally substituted independently with one or more substituents described herein. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms, and in another embodiment two to six carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), 1-propenyl, 1-buten-1-yl, 1-buten-2-yl, and the like.

The term "alkynyl" as used herein refers to a linear or branched monovalent hydrocarbon radical of two to twelve carbon atoms, and in another embodiment two to six carbon atoms, with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —$CH_2$C≡CH).

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

"Amino" means primary (i.e., —NH$_2$), secondary (i.e., —NRH), tertiary (i.e., —NRR) and quaternary (i.e., —N$^+$RRRX$^-$) amines, that are optionally substituted, in which R is independently alkyl, alkoxy, a cycloalkyl, a heterocyclyl, cycloalkyl, -substituted alkyl or heterocyclyl-substituted alkyl wherein the alkyl, alkoxy, cycloalkyl and heterocyclyl are as defined herein Particular secondary and tertiary amines are alkylamine, dialkylamine, arylamine, diarylamine, aralkylamine and diaralkylamine wherein the alkyls and aryls are as herein defined and independently optionally substituted. Particular secondary and tertiary amines are methylamine, ethylamine, propylamine, isopropylamine, phenylamine, benzylamine dimethylamine, diethylamine, dipropylamine and diisopropylamine.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms, and in another embodiment three to eight carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, cyclohexenyl, cyclohexadienyl, cycloheptenyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently with one or more substituents described herein.

The term "aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "hetercyclyl" and "heterocyclic ring" as used herein are used interchangeably and refer to a saturated or partially unsaturated carbocyclic radical of 3 to 12 membered ring atoms in which at least one ring atom is a heteroatom independently selected from nitrogen, oxygen and sulfur, the remaining ring atoms being C, where one or more ring atoms may be optionally substituted independently with one or more substituents described below. One embodiment includes heterocycles of 3 to 7 membered ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

"Leaving group" refers to a portion of a first reactant in a chemical reaction that is displaced from the first reactant in the chemical reaction. Examples of leaving groups include, but are not limited to, hydrogen, halogen, hydroxyl groups, sulfhydryl groups, amino groups (for example —NRR, wherein R is independently alkyl, alkenyl, alkynyl, cycloalkyl, phenyl or heterocyclyl and R is independently optionally substituted), silyl groups (for example —SiRRR, wherein R is independently alkyl, alkenyl, alkynyl, cycloalkyl, phenyl or heterocyclyl and R is independently optionally substituted), —N(R)OR (wherein R is independently alkyl, alkenyl, alkynyl, cycloalkyl, phenyl or heterocyclyl and R is independently optionally substituted), alkoxy groups (for example —OR, wherein R is independently alkyl, alkenyl, alkynyl, cycloalkyl, phenyl or heterocyclyl and R is independently optionally substituted), thiol groups (for example —SR, wherein R is independently alkyl, alkenyl, alkynyl, cycloalkyl, phenyl or heterocyclyl and R is independently optionally substituted), sulfonyloxy groups (for example —OS(O)$_{1-2}$R, wherein R is independently alkyl, alkenyl, alkynyl, cycloalkyl, phenyl or heterocyclyl and R is independently optionally substituted), sulfamate groups (for example —OS(O)$_{1-2}$NRR, wherein R is independently alkyl, alkenyl, alkynyl, cycloalkyl, phenyl or heterocyclyl and R is independently optionally substituted), carbamate groups (for example —OC(O)$_2$NRR, wherein R is independently alkyl, alkenyl, alkynyl, cycloalkyl, phenyl or heterocyclyl and R is independently optionally substituted), and carbonate groups (for example —OC(O)₂RR, wherein R is independently alkyl, alkenyl, alkynyl, cycloalkyl, phenyl or heterocyclyl and R is independently optionally substituted). Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)). Other examples of leaving groups include substituted and unsubstituted amino groups, such as amino, alkylamino, dialkylamino, hydroxylamino, alkoxylamino, N-alkyl-N-alkoxyamino, acylamino, sulfonylamino, and the like.

"Amino-protecting group" as used herein refers to groups commonly employed to keep amino groups from reacting during reactions carried out on other functional groups. Examples of such protecting groups include carbamates, amides, alkyl and aryl groups, imines, as well as many N-heteroatom derivatives which can be removed to regenerate the desired amine group. Particular amino protecting groups are Ac (acetyl), trifluoroacetyl, phthalimide, Bn (benzyl), Tr (triphenylmethyl or trityl), benzylidenyl, p-toluenesulfonyl, Pmb (p-methoxybenzyl), Boc (tert-butyloxycarbonyl), Fmoc (9-fluorenylmethyloxycarbonyl) and Cbz (carbobenzyloxy). One example includes Ac (acetyl), trifluoroacetyl, phthalimide, Bn (benzyl), Tr (triphenylmethyl or trityl), benzylidenyl, p-toluenesulfonyl, Pmb (p-Methoxybenzyl), Fmoc (9-Fluorenylmethyloxycarbonyl) and Cbz (Carbobenzyloxy). Further examples of these groups are found in: Wuts, P. G. M. and Greene, T. W. (2006) Frontmatter, in Greene's Protective Groups in Organic Synthesis, Fourth Edition, John Wiley & Sons, Inc., Hoboken, N.J., USA. The term "protected amino" refers to an amino group substituted with one of the above amino-protecting groups.

The term "substituted" as used herein means any of the above groups (e.g., alkyl, alkylene, alkenyl, alkynyl, cycloalkyl, aryl, heterocyclyl and heteroaryl) wherein at least one hydrogen atom is replaced with a substituent. In the case of an oxo substituent ("=O") two hydrogen atoms are replaced. "Substituents" within the context of this invention include, but are not limited to, halogen, hydroxy, oxo, cyano, nitro, amino, alkylamino, dialkylamino, alkyl, alkenyl, alkynyl, cycloalkyl, alkoxy, substituted alkyl, thioalkyl, haloalkyl (including perhaloalkyl), hydroxyalkyl, aminoalkyl, substituted alkenyl, substituted alkynyl, substituted cycloalkyl, aryl, substituted aryl, heteroaryl, substituted heteroaryl, heterocycle, substituted heterocycle, —NR$^e$R$^f$, —NR$^e$C(=O) R$^f$, —NR$^e$C(=O)NR$^e$R$^f$, —NR$^e$C(=O)OR$^f$—NR$^e$SO₂R$^f$, —OR$^e$, —C(=O)R$^e$—C(=O)OR$^e$, —C(=O)NR$^e$R$^f$, —OC(=O)NR$^e$R$^f$, —SR$^e$, —SOR$^e$, —S(=O)₂R$^e$, —OS(=O)₂R$^e$, —S(=O)₂OR$^e$, wherein R$^e$ and R$^f$ are the same or different and independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycle, substituted heterocycle.

The term "halo" or "halogen" as used herein means fluoro, chloro, bromo or iodo.

The term "a" as used herein means one or more.

Reference to "about" a value or parameter herein includes (and describes) embodiments that are directed to that value or parameter per se and in one embodiment plus or minus 20% of the given value. For example, description referring to "about X" includes description of "X".

"Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. One example of tautomers described herein includes the two tautomers of compounds of formula IV and IVa below.

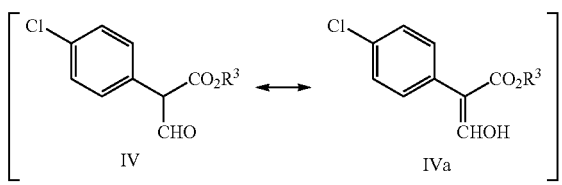

Additional specific tautomers include ethyl 2-(4-chlorophenyl)-3-hydroxyacrylate and ethyl 2-(4-chlorophenyl)-3-oxopropanoate.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

One aspect includes a process that includes reducing a compound of formula II or a salt thereof:

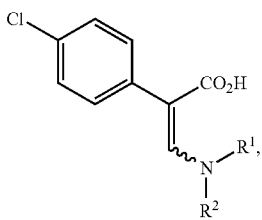

wherein:

$R^1$ and $R^2$ are independently hydrogen, $C_1$-$C_{12}$ alkyl or an amino protecting group; to form a compound of formula I:

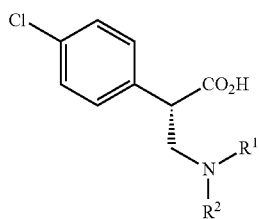

or a salt thereof.

In certain embodiments, the process of reducing a compound of formula II comprises reducing a compound of formula IIb or a salt thereof to form a compound of formula I or a salt thereof:

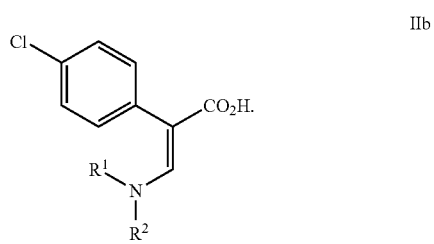

In certain embodiments, the process of reducing a compound of formula II comprises reducing a compound of formula IIa or a salt thereof to form a compound of formula I or a salt thereof:

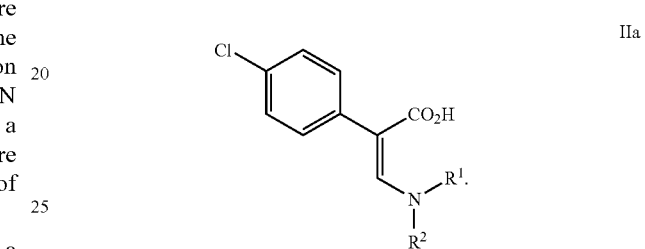

In certain embodiments of formulas II, IIa, or IIb, $R^1$ is isopropyl and $R^2$ is an amino protecting group, e.g., Boc group.

In certain embodiments, the reducing comprises contacting a compound of formula II, IIa, or IIb, or a salt thereof, with a reducing agent.

Reducing agents (e.g., used in the preparation of a compound of formula I) comprise a reducing agent capable of reducing an alkene. In one embodiment, the reducing agent comprises metal hydride (e.g., a boron, aluminum or lithium/aluminum hydride or an alkoxy- or thioalkyl-lithium aluminum hydride, such as $LiAlH(OR)_3$ where R is independently an alkyl, for example $LiAlH(OMe)_3$, $LiAlH(SMe)_3$, or $LiAlH(Otbutyl)_3$) reducing agent.

In another embodiment, the reducing agent promotes asymmetric reduction (e.g., of the alkene of formula II, IIa, or IIb, to formula I). The reducing agent may contain one or more compounds or components, such as when a reagent that is capable of hydrogen or hydride transfer is used in conjunction with an agent that promotes or directs stereoselectivity of the hydrogen or hydride transfer reaction, e.g., a stereoselective catalyst or enzyme. Thus, in one aspect, the reducing agent comprises a stereoselective reducing reagent comprising an agent that is capable of hydrogen or hydride transfer and an agent that promotes or directs stereoselectivity of the hydrogen or hydride transfer reaction. In one aspect, the agent that promotes or directs stereoselectivity of the hydrogen or hydride transfer reaction comprises transition metal catalyst. In one aspect, the agent that promotes or directs stereoselectivity of the hydrogen or hydride transfer reaction comprises an enzyme.

In certain embodiments, the reducing agent comprises a metal catalyst and hydrogen source. In certain embodiments, the metal catalyst comprises a ruthenium, rhodium, or palladium catalyst. In certain embodiments, the metal catalyst comprises [(S)-BINAPRuCl(benzene)]Cl.

Sources of hydrogen include hydrogen gas, and other sources used in transfer hydrogenation reactions, including water (optionally with formate or acetate salts such as sodium formate), diimide, hydrazine (or hydrazine hydrate), alcohols, such as methanol, ethanol and isopropanol, cycloalkenes, such as cyclohexene, cyclohexadiene, dihydronaphthalene and dihydroanthracene, organic acids (optionally with an amine such as trimethyl or triethylamine), such as formic acid, acetic acid or phosphoric acid, silanes such as $HSiR_3$ (where R is independently an alkyl group, such as $HSiMe_3$ and $HSiEt_3$), NADH, NADPH, $FADH_2$, ammonium salts, such as ammonium formate and ammonium chloride, and Hanztch esters such as those of the formula:

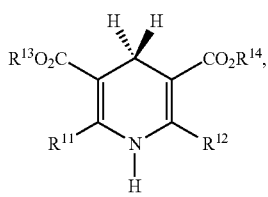

wherein $R^{11}$, $R^{12}$, $R^{13}$ and $R^{14}$ are independently alkyl (In certain examples: $R^{11}$ and $R^{12}$ are methyl and $R^{13}$ and $R^{14}$ are ethyl; $R^{11}$ and $R^{12}$ are methyl and $R^{13}$ and $R^{14}$ are butyl; $R^{11}$ is methyl, $R^{12}$ is isopropyl and $R^{13}$ and $R^{14}$ are methyl; $R^{11}$ and $R^{12}$ are methyl, $R^{13}$ is methyl and $R^{14}$ is t-butyl; $R^{11}$ and $R^{12}$ are methyl and $R^{13}$ and $R^{14}$ are methyl; $R^{11}$ and $R^{12}$ are methyl and $R^{13}$ and $R^{14}$ are isobutyl; $R^{11}$ and $R^{12}$ are methyl and $R^{13}$ and $R^{14}$ are allyl.

In certain embodiments, the reaction of a compound of formula II, IIa, or IIb, or a salt thereof, with a reducing agent to provide a compound of formula I, or a salt thereof, is carried out by a catalytic reduction reaction wherein the catalyst comprises a metal catalyst such as a ruthenium catalyst, a rhodium catalyst or a palladium catalyst to produce one or more chiral centers. Examples of metal catalysts include, but are not limited to, $RuL_3X$ (wherein X is a halogen, e.g., Cl) or $RhL_3Cl$, wherein L is a phosphine ligand, such as $PR_3$, wherein R is independently alkyl, alkenyl, alkynyl, cycloalkyl, aryl or heterocyclyl, and wherein R is independently optionally substituted, such as $[RhCl(PPh_3)_3]$.

Examples of ligands for the metal catalyst include, but are not limited to DIOP, DIPAMP, BINAP, TolBINAP, XylBINAP, BPPFOH, BPPM, BICHEP, BPPFOH, BICHHEP, BIPHEP, BIPHEMP, MeO-BIPHEP, MOD-DIOP, CyDIOP, BCPM, MCCPM, NORPHOS, PYRPHOS (DEGUPHOS), BDPP (SKEWPHOS), Me-DuPhos, Et-DuPhos, iPr-DuPhos, Me-BPE, Et-BPE, iPr-BPE, o-Ph-HexaMeO-BIPHEP, RoPHOS, KetalPhos, BASPHOS, Me-PennPhos, BINAPHANE, BICP, DIOP, BDPMI, T-Phos, SK-Phos, EtTRAP, PrTRAP, PrTRAP, BuTRAP, PhTRAP, Josiphos, PPF-tBu$_2$, Xyliphos, FerroPHOS, FERRIPHOS, TaniaPhos, f-KetalPHos, Et-FerroTANE, t-Bu-BISP, Ad-BisP, Cy-BisP, t-Bu-MiniPhos, Cy-MiniPhos, iPr-MiniPhos, TangPhos, BIPNOR, Binapine, unsymmetrical BisP, [2,2]PHANEPHOS, Ph-o-NAPHOS, spirOP, BINAPO, Ph-o-BINAPO, DIMOP, and others described in Chi, Y, et. al, Modern Rhodium-Catalyzed Organic Reactions, Ed. Evans, P.A., Wiley, 2005, Chapter 1. Examples of metal catalysts include, but are not limited to [(S)-BINAPRuCl(benzene)]Cl, [(R,R) TsDACH Ru(p-cymene)Cl] and [(R,R)Teth-TsDPEN RuCl] or (R,R)Me$_2$NSO$_2$DPEN with [RhCp*Cl$_2$]$_2$. In another example, the catalyst is a heterogeneous hydrogenation catalyst for example palladium on carbon or palladium on aluminum oxide. In one example, the catalyst is 5% Pd/C Type A405038 or 5% Pd/Al$_2$O$_3$ Type A302011 to produce the cis isomer. Other suitable catalyst may be identified by screening, e.g., based on desired stereoselectivity, reaction rate and turnover. The reducing agent may comprise any suitable hydrogen source or hydride source, such as formic acid or a boron reducing agent or hydrogen gas.

In some examples, the hydrogen source is used in combination with a metal catalyst comprising magnesium, sodium, ruthenium(II), rhodium(III), iridium(III), nickel, platinum, palladium or a combination thereof.

Another aspect includes the compound of formula I or a salt thereof produced according to the process comprising reducing a compound of formula II, IIa, or IIb, a salt thereof.

Another embodiment includes a process that includes hydrolysing a compound of formula III, or salt thereof:

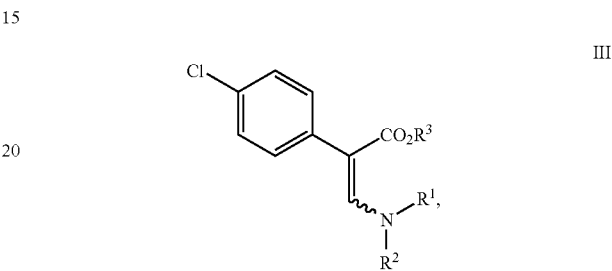

wherein:
$R^3$ is optionally substituted $C_1$-$C_{12}$ alkyl to form a compound of formula II or a salt thereof.

In certain embodiments, the process of hydrolyzing a compound of formula III, or salt thereof, to form a compound of formula II or a salt thereof comprises hydrolysing a compound of formula IIIa, or salt thereof.

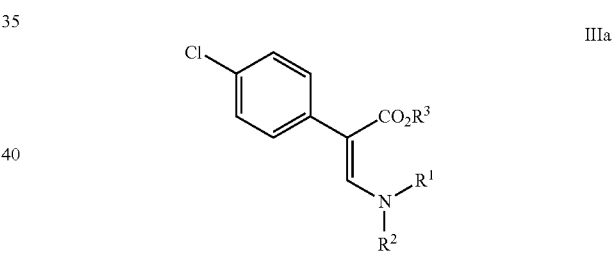

In certain embodiments, the process of hydrolyzing a compound of formula III, or salt thereof, to form a compound of formula II or a salt thereof comprises hydrolysing a compound of formula IIIb, or salt thereof.

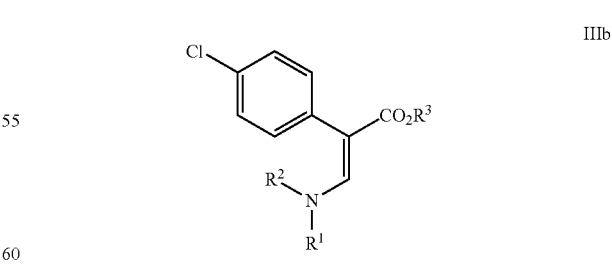

In certain embodiments, the process of hydrolyzing a compound of formula III, or a salt thereof, to form a compound of formula II or a salt thereof comprises contacting a compound of formula III, or a salt thereof, with aqueous base. Aqueous base includes, for example, a mixture of base and water. Base used for the hydrolysis includes hydroxide base. Examples of hydroxide base for the hydrolysis include sodium hydroxide, potassium hydroxide and ammonium hydroxide. The hydrolyzing reaction optionally further comprises co-solvents to facilitate the reaction, including ethers, such as tetrahydrofuran and MTBE, and alcohols, such as methanol, ethanol, isopropanol, butanol and t-butyl alcohol, and combinations thereof. In certain embodiments, the hydrolyzing reaction is conducted in a mixture of ether, alcohol and water, for example, a mixture of THF, methanol and water (for example, a mixture of each in equal parts by volume).

Another aspect includes the compound of formula II or a salt thereof produced according to the process comprising hydrolysing a compound of formula III, or salt thereof.

Another embodiment includes a process comprising reacting a compound of formula IV, or a salt or tautomer thereof:

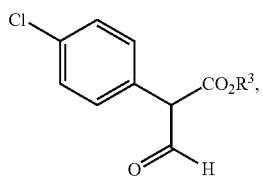

IV with —$NHR^1R^2$ or a salt thereof, to form a compound of formula III, or a salt thereof.

In certain embodiments, the compound —$NHR^1R^2$ is —$NH(C_1-C_{12}$ alkyl). In certain embodiments, the compound —$NHR^1R^2$ is $NH_3$ or a salt thereof. In certain embodiments, the compound —$NHR^1R^2$ is a salt of $NH_3$ selected from formate, carbonate, hydroxide, acetate, bromide, carbamate, sulfate, chloride, fluoride, nitrate, phosphate and thiosulfate. In certain embodiments, the compound —$NHR^1R^2$ is ammonium formate. In certain embodiments, the compound —$NHR^1R^2$ is —NH(isopropyl).

Another aspect includes the compound of formula III or a salt thereof produced according to the process comprising reacting a compound of formula IV, or a salt or tautomer thereof with —$NHR^1R^2$ or a salt thereof.

Another embodiment includes a process comprising contacting a compound of formula V or a salt thereof:

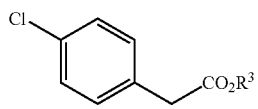

V with $HCO_2R^4$, wherein $R^4$ is optionally substituted $C_1-C_{12}$ alkyl, or a salt thereof, under basic conditions, to form a compound of formula IV, or a salt thereof In certain embodiments, $R^4$ is $C_1-C_6$ alkyl. In certain embodiments, $R^4$ is ethyl.

In certain embodiments, the basic conditions include a non-nucleophilic base. In certain embodiments, the base comprises hydroxide, alkoxide, lithium alkyl bases or lithium amide bases. In certain embodiments, the base comprises lithium diisopropylamide, t-butyl lithium, sodium t-butoxide, potassium t-butoxide, ammonium t-butoxide, sodium hydroxide, potassium hydroxide or ammonium hydroxide. In certain embodiments, the base comprises potassium t-butoxide. In certain embodiments, the basic conditions further comprise a solvent such as a polar solvent, selected from alcohols, ethers, amides or other suitable solvents or combinations thereof. For example, ether or alcohol solvents are used, such as diethyl ether, MTBE, methanol, ethanol or isopropanol. In one example, the solvent is MTBE.

Another aspect includes the compound of formula IV or salt thereof produced according to the process comprising contacting a compound of formula V or a salt thereof with $HCO_2R^4$, wherein $R^4$ is optionally substituted $C_1-C_{12}$ alkyl, or a salt thereof, under basic conditions.

Another embodiment includes a compound of formula VI:

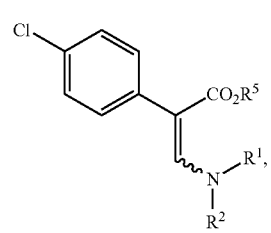

VI or salt thereof, wherein:

$R^1$ and $R^2$ are independently hydrogen, $C_1-C_{12}$ alkyl or an amino protecting group; and $R^5$ is hydrogen or an optionally substituted $C_1-C_{12}$ alkyl.

In certain embodiments of formula VI, $R^1$ is hydrogen or t-butyloxycarbonyl; $R^2$ is $C_1-C_{12}$ alkyl; and $R^5$ is hydrogen or $C_1-C_{12}$ alkyl.

In certain embodiments of formula VI, $R^1$ is hydrogen; $R^2$ is isopropyl; and $R^5$ is hydrogen or ethyl.

In certain embodiments, the compound of formula VI includes a compound of the formula VIa:

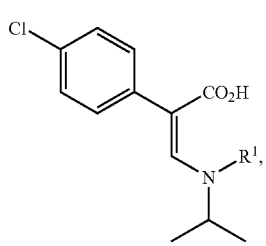

VIa or a salt thereof wherein $R^1$ is hydrogen or an amino protecting group.

In certain embodiments, the compound of formula VI includes a compound of the formula VIb:

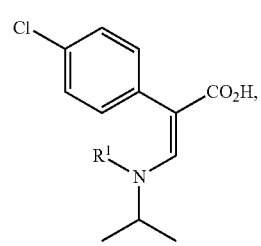

VIb or a salt thereof wherein $R^1$ is hydrogen or an amino protecting group.

In certain embodiments, $R^1$ in formula Va is t-butyloxycarbonyl. In certain embodiments, $R^1$ in formula Va is hydrogen.

In certain embodiments of formulas I-III and VI, $R^1$ is an amino protecting group.

In certain embodiments of formulas I-III and VI, $R^2$ is an amino protecting group. In certain embodiments, $R^1$ and $R^2$ are independently an amino protecting group. In certain embodiments, $R^2$ is Boc amino protecting group. In certain embodiments, $R^1$ and $R^2$ are Boc amino protecting group.

In certain embodiments of formulas I-III and VI, $R^2$ is $C_1$-$C_{12}$ alkyl. In certain embodiments, $R^1$ is hydrogen and $R^2$ is $C_1$-$C_{12}$ alkyl.

In certain embodiments of formulas I-III and VI, $R^2$ is isopropyl. In certain embodiments, $R^1$ is hydrogen and $R^2$ is isopropyl. In certain embodiments, $R^1$ is hydrogen and $R^2$ is amino protecting group. In certain embodiments, $R^1$ is hydrogen and $R^2$ is Boc amino protecting group.

In certain embodiments of formulas I-III and VI, $R^1$ is tert-butyloxycarbonyl and $R^2$ is isopropyl.

In certain embodiments of formulas I-III and VI, $R^1$ and $R^2$ are tert-butyloxycarbonyl.

In certain embodiments, the amino protecting group is selected from acetyl, trifluoroacetyl, phthalimide, benzyl, triphenylmethyl, benzylidenyl, p-toluenesulfonyl, p-methoxybenzyl, tert-butyloxycarbonyl, 9-fluorenylmethyloxycarbonyl and carbobenzyloxy.

The compounds detailed herein may contain one or more chiral centers. Accordingly, if desired, such compounds can be prepared or isolated as pure stereoisomers (such as individual enantiomers or diastereomers, or as stereoisomer-enriched mixtures). All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic or stereoisomer-enriched mixtures of such compounds can be separated using, for example, chiral column chromatography, chiral resolving agents, and the like.

Compounds detailed herein may be present as mixtures of configurational or cis/trans isomers. For example, compounds of formulas II, III and VI comprise mixtures of (E) and (Z) isomers, as denoted by the wavy line. For example, compounds of formula II include mixtures of formula IIa (the (Z) isomer) and IIb (the (E) isomer), unless described otherwise, as shown below.

For illustrative purposes, Scheme 1 shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Scheme and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

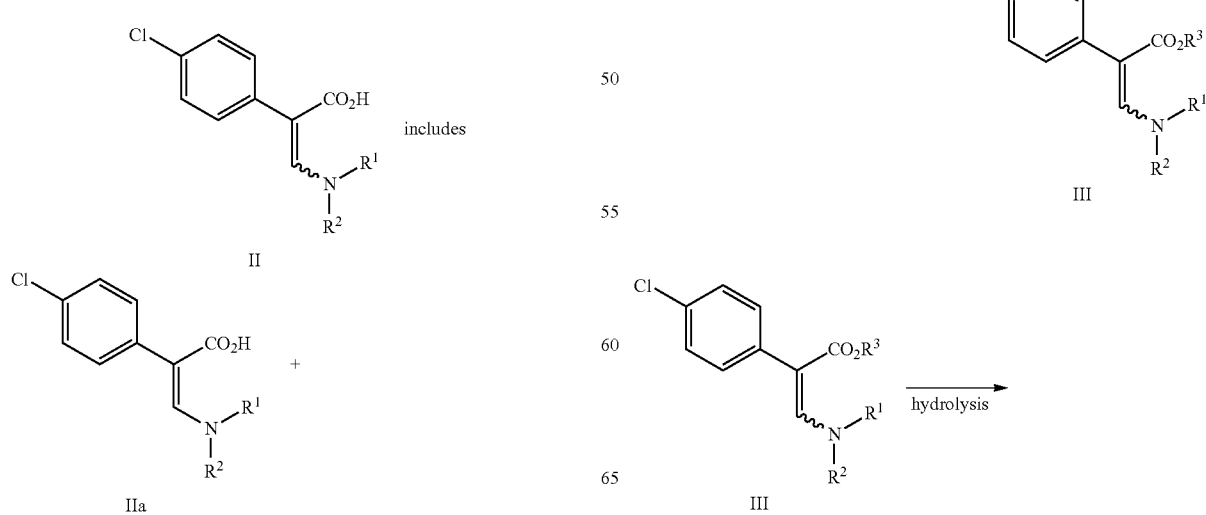

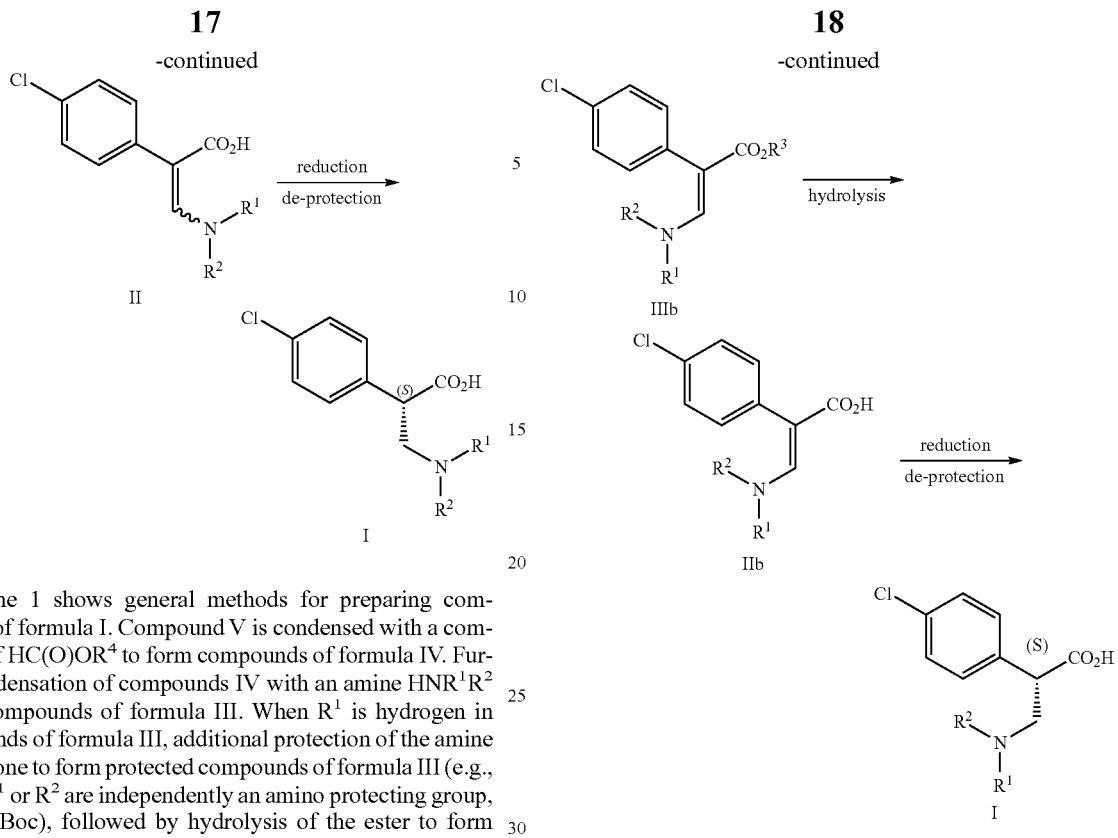

Scheme 1 shows general methods for preparing compounds of formula I. Compound V is condensed with a compound of HC(O)OR⁴ to form compounds of formula IV. Further condensation of compounds IV with an amine HNR¹R² forms compounds of formula III. When R¹ is hydrogen in compounds of formula III, additional protection of the amine can be done to form protected compounds of formula III (e.g., where R¹ or R² are independently an amino protecting group, such as Boc), followed by hydrolysis of the ester to form compounds of formula II. Asymmetric reduction of compounds of formula II gives compounds of formula I. Optional further deprotection of compound of formula I, when R¹ and/or R² is an amino protecting group, e.g., a Boc group, leads to compounds of formula I, wherein R¹ and/or R² are hydrogen.

Scheme 2 shows alternative general methods for preparing compounds of formula I, wherein the (E)-isomer of compounds IIIb and IIb are used.

Another aspect provides the use of compounds of formula I as intermediates for preparing pharmaceutically active compounds, such as the AKT inhibitors described in U.S. Pat. No. 8,063,050, issued Nov. 22, 2011 to Mitchell et al. For example, as shown below in Scheme 2, compounds of formula I can be used to prepare (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one, as described in U.S. Pat. No. 8,063,050, issued Nov. 22, 2011, as described, for example, in Example 14, which is incorporated herein by reference.

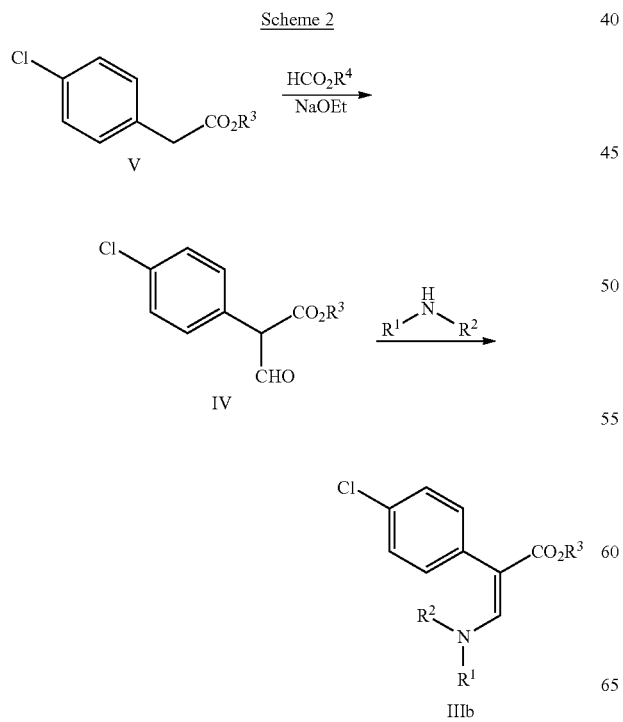

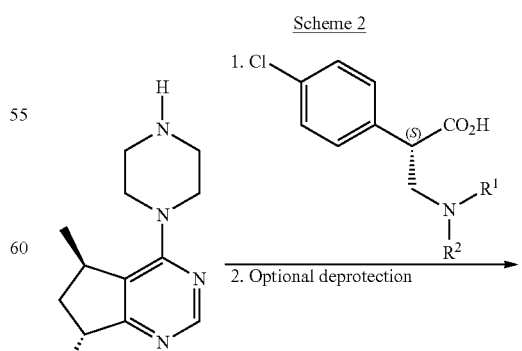

-continued

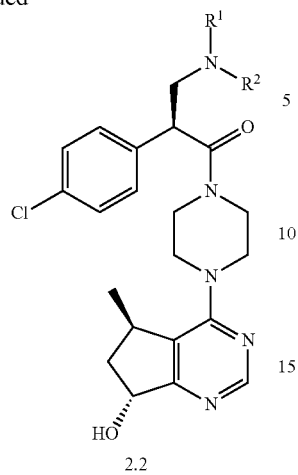

2.2

Scheme 2 illustrates a method for making a compound of formula 2.2. Compounds of formula 2.1, prepared as described in U.S. Pat. No. 8,063,050, can be acylated with a compound of formula I, for example where $R^1$ is isopropyl and $R^2$ is Boc, to give an amide, which after optional functionalisation, such as by deprotecting the Boc group, for example, gives compounds of formula 2.2, such as (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one where $R^1$ is isopropyl and $R^2$ is hydrogen.

Another aspect includes a process of producing a compound of formula 2.2, or salt thereof,

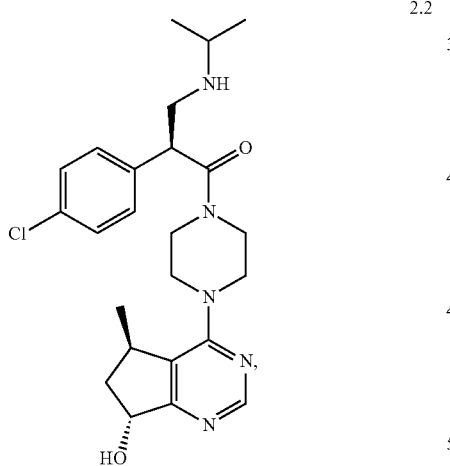

2.2 comprising reacting a compound of formula 2.1, or salt thereof,

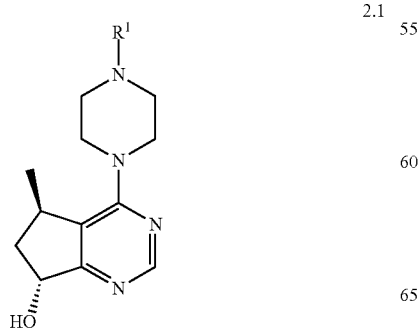

2.1 with a compound of formula Ia

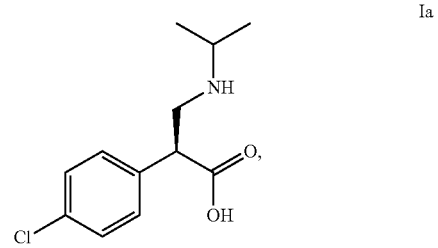 [SMILES: CC(C)NC[C@@H](C(=O)O)c1ccc(Cl)cc1]

Ia or salt thereof, to form a compound of formula 2.2.

Another aspect includes the compound of formula 2.2 or salt thereof produced according to the process comprising reacting a compound of formula 2.1, or salt thereof, with a compound of formula Ia, or salt thereof.

Compositions comprising a compound as detailed herein, or salt thereof, are also embraced by the invention. In one aspect, a composition comprising a compound of formula VI, or a salt thereof, is provided. In a particular variation, the composition comprises a salt of a compound of formula VIa. In a particular variation, the composition comprises a salt of a compound of formula VIb.

EXAMPLES

The invention can be further understood by reference to the following examples, which are provided by way of illustration and are not meant to be limiting.

Abbreviations used herein are as follows:
AcOH: Acetic Acid
Aq.: aqueous
DIPA: diisopropylamine
DIPEA: diisopropylethylamine
MTBE: methyl t-butyl ether
MsDPEN: N-methanesulfonyl-1,2-diphenylethylenediamine
TsDACH: N-(p-toluenesulfonyl)-1,2-diaminocyclohexane
Dppp: 1,3-Bis(diphenylphosphino)propan
PhME: toluene
DBU: 1,8-Diazobicyclo[5,40]undec-7-ene Example 1

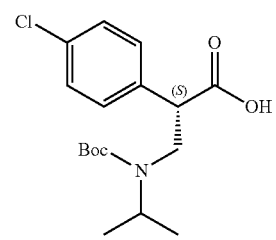

(S)-3-(tert-butoxycarbonyl(isopropyl)amino)-2-(4-chlorophenyl)propanoic acid (E)-ethyl 3-((tert-butoxycarbonyl)(isopropyl)amino)-2-(4-chlorophenyl)acrylate Into a solution of ethyl formate (123.9 L, 1538.9 mol) in MTBE (189 L) was added ethyl 4-chlorophenylacetate (120 kg, 604.1 mol). The mixture was stirred at 15-30° C. for 30 min and then a mixture of t-BuOK (136.8 kg, 1219.1 mol) in MTBE (1215.8 L) was added while maintaining the internal temperature below 5° C. The mixture was stirred between 0-10° C. for 1.5 h. The reaction mixture was added to an aqueous solution of hydrochloric acid (35%, 99.8 L in 560 L H$_2$O) maintaining the internal temperature below 10° C. The mixture was stirred for 30 min between 0-10° C. until a final pH=2 was observed. The layers were separated and the organic layer was washed with 25% NaCl solution (496 L). The mixture was cooled to −5° C. and then isopropylamine (107.2 L, 1251.9 mol) and AcOH (70.5 L, 1233.3 mol) were slowly added maintaining the temperature <10° C. The mixture was stirred for 3 h at 0-10° C. and then the organic layer was washed with H$_2$O (760 L), 15% aqueous Na$_2$CO$_3$ (424 L) and then 25% aqueous NaCl (650 L). The aqueous layer was separated and DMF (443 L) and DMAP (14.4 kg. 117.9 mol) were added to the organic solution. The mixture was then heated to 60-65° C. followed by slow addition of (Boc)$_2$O (951.6 L, 4142 mol), DMF (228.6 L) and triethylamine (263.0 L, 1821.8 mol) over 24 h. After stirring ~6 h, the mixture was cooled to room temperature and MTBE (1434 L), water (1010 L) and 10% aqueous citric acid (938 L) were added. The aqueous layer was separated and the mixture was washed by 25% aqueous NaCl (984 L). The organic layer was then concentrated via distillation to a minimum working volume (~240 L) while maintaining the temperature below 50° C. The organic layer was then stirred for 5 h at 0-5° C. and filtered. The filter cake was washed with heptane (20.6 L) and dried to afford (E)-ethyl 3-((tert-butoxycarbonyl)(isopropyl)amino)-2-(4-chlorophenyl)acrylate (148.55 kg, 63% yield over three steps) as a white solid.

(E)-3-(tert-butoxycarbonyhisopropyl)amino)-2-(4-chlorophenyl)acrylic acid (E)-ethyl 3-((tert-butoxycarbonyl)(isopropyl)amino)-2-(4-chlorophenyl)acrylate (133.5 kg, 362.9 mol) was added into a mixture of H$_2$O (252 L), NaOH (58.25 kg, 1456 mol) and EtOH (383.5 L) stirred at room temperature. The mixture was warmed to 40-45° C. for 2.5 h until a clear solution was formed. The mixture was concentrated to a minimum working volume maintaining the temperature below 50° C. The mixture was then cooled to 10-25° C. and a solution of HCl was added (842 L of 2N HCl and 11 L of 35% HCl) until a final pH=2~4 was obtained. The aqueous layer was separated and the organic layer was washed with 25% aqueous NaCl (810 L). n-Heptane was added while distilling to form a suspension. The product was collected and washed with n-heptane and dried at 40-45° C. for ~10 h to afford 110.7 kg (90.5% yield) of (E)-3-(tert-butoxycarbonyl(isopropyl) amino)-2-(4-chlorophenyl)acrylic acid having 99.9 A % purity by HPLC. E-configuration was confirmed using single crystal x-ray analysis (See FIG. 1).

(S)-3-(tert-butoxycarbonyl(isopropyl)amino)-2-(4-chlorophenyl)propanoic acid

Into a thoroughly cleaned reactor was charged (E)-3-(tert-butoxycarbonyl(isopropyl)amino)-2-(4-chlorophenyl) acrylic acid (33 kg, 84.7 mol), EtOH (164.6 L), LiBF$_4$ (0.462 kg, 4.9 mol) and [(S)-BINAPRuCl(benzene)]Cl (0.043 kg, 0.049 mol) were added. The mixture was degassed and then stirred for 24-26 h under hydrogen (3.0-3.5 MPa) until IPC by HPLC showed no starting material remained.

A solution of compound (S)-3-(tert-butoxycarbonyl(isopropyl)amino)-2-(4-chlorophenyl)propanoic acid (~20% assay in EtOH solution 138.7 kg in 680 kg EtOH) was concentrated to 139-277 L below 50° C. to which was added EtOAc (999 L). The mixture was washed with 25% aqueous NaCl (700 L×3) and then the organic layer concentrated to 555-694 L below 50° C. To the solution was added silica thiol (8.30 kg) and the mixture was stirred for 14 h at 45-50° C. After cooling to 10-30° C., the mixture was filtered and washed with EtOAc (40 L). The filtrate was concentrated to 139 L below 50° C. and n-heptane (485 L×2) was added in portions with continuous distillation to form a suspension. The suspension was stirred for 1.5 h at 45-50° C. and stirred for 12-16 h at −5 to 5° C. The product was collected by filtration and washed with n-heptane (229 L×4). The filter cake was dried for 10 h at 40-45° C. to afford compound (S)-3-(tert-butoxycarbonyl(isopropyl)amino)-2-(4-chlorophenyl)propanoic acid (126.29 kg, 91% yield and >99% ee) as a white solid. $^1$H NMR (400 MHz, MeOH-d$_4$) δ 7.33 (s, 4H), 3.7-3.73 (3H), 3.44 (s, 1H), 1.44 (s, 9H), 1.07-1.09 (d, 3H), 0.96-0.98 (d, 3H).

Example 2

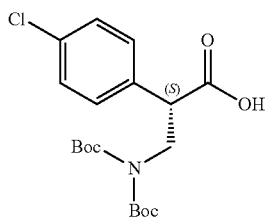

(S)-3-((bis-tert-butoxycarbonyl)amino)-2-(4-chlorophenyl)propanoic acid

Ethyl 2-(4-chlorophenyl)-3-oxopropanoate

To an oven-dried, round bottom flask purged with nitrogen containing a solution of 4-ethyl 2-(4-chlorophenyl)acetate (100 g, 0.51 mol, 1.0 equiv) in MTBE (1.0 L, 10 vol), was added the t-BuOK (113.0 g, 1.0 mol, 2.0 equiv) portionwise at 0° C. The reaction mixture was stirred for 15 min at 0° C. and then ethyl formate (101.7 mL, 1.3 mol, 2.5 equiv) was added dropwise. Reaction was monitored by HPLC (IPC by LCMS (m/z): [M]$^+$ shows 226.9). The reaction mixture was stirred at 0-10° C. for 3 h then quenched into the cold 2N aqueous HCl. The organic phase was separated and washed with brine (3×300 mL). Concentration of the organic phase under reduced pressure afforded the crude product (91 g, 81% yield) as an unassigned mixture of the isomers (~1:1 mixture of ethyl 2-(4-chlorophenyl)-3-oxopropanoate/ethyl 2-(4-chlorophenyl)-3-hydroxyacrylate) and brown oil. The crude product mixture was used directly for next step without further purification.

Ethyl 3-amino-2-(4-chlorophenyl)acrylate

A ~1:1 mixture of ethyl 2-(4-chlorophenyl)-3-oxopropanoate/ethyl 2-(4-chlorophenyl)-3-hydroxyacrylate (50.0 g, 0.22 mol, 1.0 equiv) and ammonium formate (69.6 g, 1.10 mol, 5.0 equiv) in EtOH (500 mL, 10 vol) was heated at 65° C. for 8 h. Reaction was monitored by HPLC (IPC by LCMS (m/z): [M]$^+$ shows 225.9). The reaction mixture was then concentrated under reduced pressure to a minimal working volume. The mixture was partitioned between cold water (200 mL) and EtOAc (200 mL). The organic phase was separated and washed with saturated aqueous NaHCO$_3$ (100 mL) and brine (3×100 mL). The organics were dried over anhydrous Na$_2$SO$_4$, filtered and concentrated to give crude product ethyl 3-amino-2-(4-chlorophenyl)acrylate (42 g, 85% yield) as an unassigned mixture of E/Z isomers (~1:1) and brown oil. The crude product was used directly for next step without further purification.

(E)-ethyl 3-((bis-tert-butoxycarbonyl)amino)-2-(4-chlorophenyl)acrylate

To the solution of ethyl 3-amino-2-(4-chlorophenyl)acrylate (63.7 g, 0.28 mol, 1.0 equiv) in DMF (382 mL, 6 vol) was charged triethylamine (85.0 g, 0.84 mol, 3.0 equiv) and DMAP (6.8 g, 0.056 mol, 0.2 equiv). A solution of Boc$_2$O (305.6 g, 1.4 mol, 5.0 equiv) and DMF (255 mL, 4 vol) was added dropwise to the flask at 65° C. over 1 h, and the resulting reaction mixture was maintained at 65° C. for ~8 h. The reaction mixture was then quenched by dropwise addition of saturated aqueous NaHCO$_3$ (130 mL) at room temperature and extracted with EtOAc (260 mL). The organics were washed with brine (3×200 mL), dried (Na$_2$SO$_4$), filtered and concentrated under reduced pressure to afford the crude product (E)-ethyl 3-((bis-tert-butoxycarbonyl)amino)-2-(4-chlorophenyl)acrylate as brown oil. Purification via chromatography (1:20, EtOAc/Petroleum ether) gave pure product (63.7 g, 53% yield) as yellow oil. $^1$H NMR (400 MHz, CDCl$_3$) δ: 7.62 (s, 1H), 7.31 (d, J=8.4 Hz, 2H), 7.18 (d, J=8.4 Hz, 2H), 4.24 (dd, J=7.2 Hz and J=14.2 Hz, 2H), 1.34 (s, 18H), 1.28 (t, J=6.8 Hz, 3H); MS-ESI (m/z): [M+Na]$^+$ 448.0.

3-((bis-tert-butoxycarbonyl)amino)-2-(4-chlorophenyl)acrylic acid

The (E)-ethyl 3-((bis-tert-butoxycarbonyl)amino)-2-(4-chlorophenyl)acrylate (73.4 g, 0.172 mol, 1.0 equiv) was stirred with NaOH (8.96 g, 0.224 mol, 1.3 equiv) in THF/MeOH/H$_2$O (1:1:1 by volume, 734 mL, 10 vol) for 10 h, and then 2N aqueous HCl was add into the flask until the pH=7 to quench the reaction. The organic solvent was removed by vacuum distillation, and the product was collected by filtration. After trituration in petroleum ether (146 mL, 2 vol), 3-((bis-tert-butoxycarbonyl)amino)-2-(4-chlorophenyl) acrylic acid (48.0 g, 70% yield) was obtained as white powder. $^1$H NMR (400 MHz, CD$_3$CN) δ: 7.54 (s, 1H), 7.37 (d, J=8.0 Hz, 2H), 7.17 (d, J=8.0 Hz, 2H), 1.31 (s, 18H); MS-ESI (m/z): [M+Na]$^+$ 420.0.

(S)-3-((bis-tert-butoxycarbonyl)amino)-2-(4-chlorophenyl)propanoic acid

To the suspension of the LiBF$_4$ (4.67 g, 0.05 mol, 1.0 equiv) and 3-((bis-tert-butoxycarbonyl)amino)-2-(4-chloro-phenyl) acrylic acid 5 (20 g, 0.05 mol, 1 equiv) in ethanol (400 mL, 20 vol), the catalyst [(S)-BINAP-RuCl(benzene)]Cl (0.44 g, 0.0005 mol, 0.01 equiv) was added under a nitrogen atmosphere. After vacuum degassing and hydrogen purging three times, the reaction mixture was stirred at 55° C. under hydrogen atmosphere (50 psi) for 24 h and filtered through Celite to remove the metal catalyst. The filtrate was concentrated to dryness under reduced pressure to afford the pure product (S)-3-((bis-tert-butoxycarbonyl)amino)-2-(4-chlorophenyl) propanoic acid (20.1 g, >99% yield and 95.9% ee) as pale solid. $^1$H NMR (400 MHz, CDCl$_3$) δ: 7.30 (s, 4H), 3.75~3.73 (m, 3H), 1.41 (s, 18H); MS-ESI (m/z): [M+Na]$^+$ 422.0.

I claim:

1. A process comprising reducing a compound of formula II, or a salt thereof:

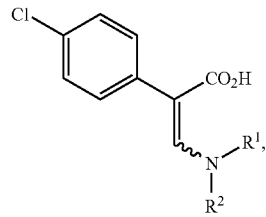

wherein:
R$^1$ and R$^2$ are independently hydrogen, C$_1$-C$_{12}$ alkyl or an amino protecting group to form a compound of formula I:

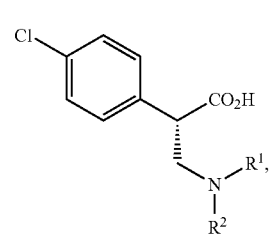

or a salt thereof.

2. The process of claim 1, further comprising hydrolyzing a compound of formula III, or salt thereof:

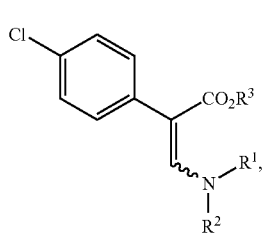

wherein:
R$^3$ is optionally substituted C$_1$-C$_{12}$ alkyl, to form a compound of formula II.

3. The process of claim 2, further comprising reacting a compound of formula IV, or a salt or tautomer thereof:

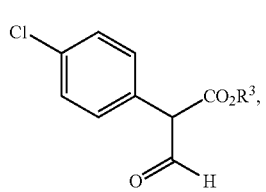

with —NHR$^1$R$^2$ or a salt thereof, to form a compound of formula III, or a salt thereof.

4. The process of claim 3, wherein NHR$^1$R$^2$ is —NH(isopropyl).

5. The process of claim 3 further comprising contacting a compound of formula V or a salt thereof:

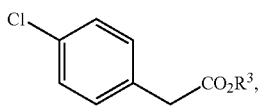

with $HCO_2R^4$, wherein $R^4$ is optionally substituted $C_1$-$C_{12}$ alkyl, or a salt thereof, under basic conditions, to form a compound of formula IV, or a salt thereof.

6. The process of claim 5, wherein said basic conditions comprise a base selected from hydroxide or alkoxide base.

7. The process of claim 1, wherein $R^1$ is an amino protecting group.

8. The process of claim 1, wherein said amino protecting group is selected from acetyl, trifluoroacetyl, phthalimide, benzyl, triphenylmethyl, benzylidenyl, p-toluenesulfonyl, p-methoxybenzyl, tert-butyloxycarbonyl, 9-fluorenylmethyloxycarbonyl and carbobenzyloxy.

9. The process of claim 1, wherein $R^1$ is tert-butyloxycarbonyl and $R^2$ is isopropyl.

10. The process of claim 1, wherein said reducing comprises contacting a compound of formula II, or a salt thereof, with a metal catalyst and hydrogen gas.

11. The process of claim 10, wherein said metal catalyst is a ruthenium, rhodium, or palladium catalyst.

12. The process of claim 10, wherein said metal catalyst is [(S)—BINAPRuCl(benzene)]Cl.

13. The process of claim 1, wherein $R^2$ is an amino protecting group.

14. The process of claim 1, wherein $R^2$ is $C_1$-$C_{12}$ alkyl.

15. The process of claim 1, wherein $R^2$ is isopropyl.

16. The process of claim 1, wherein said reducing comprises reducing a compound of formula IIb, or a salt thereof:

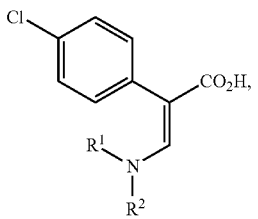

to form said compound of formula I or a salt thereof.

17. A compound of formula VI:

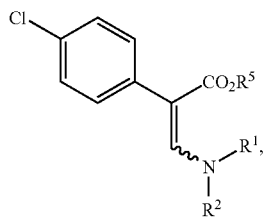

or salt thereof, wherein:
- $R^1$ is hydrogen, acetyl, trifluoroacetyl, phthalimide, benzyl, triphenylmethyl, benzylidenyl, p-methoxybenzyl, tert-butyloxycarbonyl, 9-fluorenylmethyloxycarbonyl or carbobenzyloxy;
- $R^2$ is $C_1$-$C_{12}$ alkyl; and
- $R^5$ is hydrogen or $C_1$-$C_{12}$ alkyl.

18. The compound of claim 17, wherein $R^1$ is hydrogen; $R^2$ is isopropyl; and $R^5$ is hydrogen or ethyl.

19. The compound of claim 17, having the formula VIb:

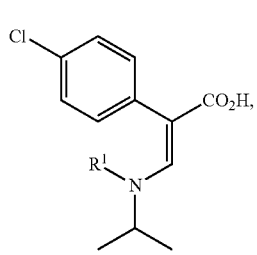

or a salt thereof wherein $R^1$ is hydrogen or t-butyloxycarbonyl.

20. The compound of claim 17, wherein $R^1$ is t-butyloxycarbonyl.

21. A compound of formula VIb:

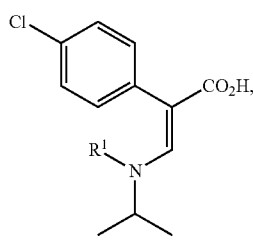

or a salt thereof wherein $R^1$ is hydrogen or an amino protecting group.

* * * * *